United States Patent [19]

Yagi et al.

[11] Patent Number: 4,756,910

[45] Date of Patent: Jul. 12, 1988

[54] ADRIAMYCIN-ENTRAPPING LIPOSOME PREPARATION

[75] Inventor: Kunio Yagi, Nagoya,/; Nakao Kojma, Kani; Makoto Takano, Ibaragi, all of Japan.

[73] Assignee: Kabushiki Kaisha Vitamin Kenkyusyo, Tokyo, Japan

[21] Appl. No.: 934,589

[22] Filed: Nov. 25, 1986

[30] Foreign Application Priority Data

Nov. 29, 1985 [JP]  Japan ................... 60-267315

[51] Int. Cl.$^4$ .......................... A61K 37/22; A61J 5/00; B01J 13/02; B32B 5/16
[52] U.S. Cl. .................................... 424/450; 424/417; 264/4.1; 264/4.3; 264/4.6; 428/402.2
[58] Field of Search ................. 424/450, 417; 264/4.1, 264/4.3, 4.6; 428/402.2

[56] References Cited

FOREIGN PATENT DOCUMENTS 8500968  3/1985  PCT Int'l Appl. ................ 424/450

OTHER PUBLICATIONS

The 26th Meeting of the Japanese Society of Neurology, May 22, 23, 24, 1985.

Primary Examiner—Albert T. Meyers
Assistant Examiner—John M. Kilcoyne
Attorney, Agent, or Firm—Armstrong, Nikaido, Marmelstein & Kubovcik

[57] ABSTRACT

A liposome preparation entrapping adriamycin as the effective component, whose constitutional lipids are phosphatidylcholine, cholesterol, and sulfatide in a specific molar ratio.

1 Claim, 2 Drawing Sheets

Peak

A: Adriamycin-entrapping liposomes with multi-layers.

B: Adriamycin-entrapping small liposomes with a single layer

C: Free adriamycin a: Liposomes with multi-layers b: Small liposomes with a single layer

ADRIAMYCIN-ENTRAPPING LIPOSOME PREPARATION

BACKGROUND OF THE INVENTION

1. Field of the Invention

The present invention relates to a liposome preparation and more particularly to that entrapping or bearing adriamycin as the effective component.

2. Related Arts

Adriamycin has widely been employed as an effective component for curing malignant tumors. Adriamycin has a positive charge at physiological pH and thus binds to cell surfaces as well as mitochondrial and other cellular membranes, particularly to phospholipids which are negatively charged. The drug shows an accumulative cardiac toxicity, and therefore the dosing amount of the drug has been limited. Further, the drug has a relatively high affinity for living tissues, so that the drug rapidly disappears from the blood after intravenous administration. Therefore, there is a little chance of the drug's being taken up by tumor tissue.

On the other hand, liposomes are the lipid vesicles and prepared by suspending a polar lipid film in an aqueous solution. The liposomes have been classified from a morphological view point into (a) small unilamellar vesicles (small liposomes with a single layer), (b) large unilamellar vesicles (large liposomes with a single layer), and (c) multi lamellar vesicles (liposomes with multi-layers). Each of these liposomes has basically the same structure as cell membranes in the living body and thus has been widely employed as a model for studying the physicochemical structure of the living cell membranes. Since 1970, studies have been made towards the application of the liposomes as vehicles or carriers of drugs or enzymes to the living body, based on the assumption that the liposomes would act as microcapsules of drugs or the like having the following advantages:

1. Protection of the encapsulated agent from various metabolic enzymes,
2. Decrease of undesired side effects appearing in other tissues,
3. Suppression of immune reactions against drugs or the like,
4. Sustentation of pharmacological effect due to slow release,
5. Improvement in arrival to target tissues.
6. Increase of amount of drugs or the like taken into cells,
7. Selective uptake into cytoplasm or lysosomes, and
8. Possibility of remote control on arrival of drugs or the like to tissues by, for instance, warming a specific part of the body from outside, thereby causing release of the contents of the liposomes.

In general, the liposomes are prepared from polar lipids such as phosphatidylcholine, which is easily available and has been extensively studied on its physical characteristics, and cholesterol, for adjusting fluidity of the layer or membrane to be formed, and, if necessary, other lipids for giving a specific organ selectivity to the liposomes. According to a conventional method, the liposomes are prepared by dissolving these lipids in organic solvents, treating the resulting solution with a rotary evaporator to evacuate the solvents and thus leave a thin lipid film on the inner surface of the glass vessel, drying the film sufficiently, adding a drug or enzyme solution to swell the film, shaking the vessel to dislodge the film, sonicating the swollen film under an inert gas atmosphere to form a liposome suspension, and removing free drug or enzyme unentrapped in the liposomes from the suspension with use of ultracentrifugation, gel-filtration method, or the like. The drug, enzyme, or the like are encapsulated in the inner space of the liposomes, and may further be embedded in layer(s) of the liposomes or be adhered to the inner and outer surfaces of the liposome membranes, depending on characteristics of the materials in a liposome preparation.

The inventors have carried out many studies to develop an advantageous method to dose anti-tumor agents inclusive of adriamycin; and as one of the studies, they tried to encapsulate adriamycin by various liposomes.

As a result, it has been found that in the case of the liposomes prepared by adding a solution of adriamycin to a lipid film consisting of phosphatidylcholine and cholesterol, the amount of adriamycin encapsulated by the liposomes can not be made so high, since there is limitation of adriamycin solubility. Therefore, they have further studied the utilization of the positive charge in adriamycin, which charge has been considered to be involved in the cardiac toxicity, but introducing various lipids having negative charges into the liposome layer, and found out that the addition of sulfatide of acidic glycolipid results in the liposomes that effectively entrap adriamycin and that the entrapped adriamycin retains its anti-tumor activity as it were. Also, when adriamycin-entrapping liposomes were given to animals, the concentration of the drug in the blood is kept at a higher level than that in the case in which adriamycin was solely dosed, so that an increased probability of the drug's being taken into tumor tissue could be expected and an accumulation of the drug in the heart can be lowered to decrease its toxicity. This was reported by them at the 26th Meeting of the Japanese Society of Neurology, which was held in Matsue City, Shimane, Japan, on May 24, 1985.

The adriamycin-entrapping liposomes reported at the Meeting had been prepared with lipids of phosphatidylcholine, cholesterol, and sulfatide in a molar ratio of 7:2:1, which has been widely employed for encapsulating drugs, enzymes, or the like. The liposomes are convenient for increasing the amount of adriamycin in the liposomes and for decreasing drug accumulation in the heart; but, as a result of further study, it has been found that this molar ratio of lipids is not always the best one. Namely, the reported liposomes cannot be said to be ones that sufficiently satisfy the following requirements of the ideal liposome preparation which provides an effective and suitable utilization of adriamycin:

(a) The amount of adriamycin entrapped in the liposomes is as large as possible; thus, the amount of lipids dosed will be at its minimum.

(b) The accumulation of adriamycin in the heart is low, so as to suppress the manifestation of cardiac toxicity as much as possible, (c) The concentration of adriamycin is kept at a level high enough to attain a stable and sustaining manifestation of its pharmacological effect, and (d) Such requirements (a) to (c) are satisfied with a good balance.

SUMMARY OF THE INVENTION

An object of the present invention is to provide an adriamycin-entrapping liposome preparation which satisfies said requirements with a good balance.

Another object of the invention is to provide an adriamycin-entrapping liposome preparation which can further increase the concentration of adriamycin in the blood.

The above objects and other objects to be appreciated can be attained by an adriamycin-entrapping liposome preparation whose constitutional lipids are phosphatidylcholine, cholesterol, and sulfatide in a molar ratio of about 5:4:1.

The molar ratio of the lipids in the liposome preparation according to the invention has been specified based on the following:

In order to maintain the desired concentration of adriamycin in the blood, it is necessary to stabilize the liposomes for preventing a break-down thereof and leakage of adriamycin therefrom into the blood. The inventors have paid attention to the fact that cholesterol has a function to stabilize the liposomes, and thus they studied firstly the amount of cholesterol among the other lipids constituting the liposomes, and found out that in the case of a low cholesterol content (phosphatidylcholine:cholesterol:sulfatide=7:2:1 as in the liposomes reported at said Meeting), the amount of adriamycin entrapped in the liposome preparation was substantially the same as that in the liposome preparation according to the invention but when it was dosed to animals, a concentration thereof in the blood became lower than that of the latter, and in the case of high cholesterol content (phosphatidylcholine:cholesterol:sulfatide=4:5:1), it was difficult to form the liposomes at temperature condition of 4° C. required to maintain the pharmacological activity of adriamycin, almost all of the liposomes prepared at room temperature have multi-layers and it was difficult to prepare small liposomes with a single layer. Therefore, it has been concluded that the preferable cholesterol content is about 40 mol % in the total lipid content. In the case of a high sulfatide content (phosphatidylcholine:cholesterol:sulfatide=4:4:2), further, it was difficult to prepare the liposomes at the temperature of 4° C. and the amount of adriamycin entrapped in multi-layered liposomes prepared at room temperature was substantially the same as that entrapped in the liposomes according to the present invention, although the sulfatide content in the former was higher than that in the latter and the concentration of adriamycin in the blood was quite low when the former liposomes were dosed. Therefore, it has been concluded that the preferable sulfatide content is about 10 mol % in the total lipid content.

Further, the inventors have prepared another type of liposomes, wherein phosphatidylserine was chosen as an acidic lipid in lieu of the sulfatide (phosphatidylcholine:cholesterol:phosphatidylserine=5:4:1) but such type liposomes showed a low content of adriamycin and when they were dosed to animals, adriamycin was accumulated in the heart to a larger extent and contrary thereto, the concentration thereof in the blood showed a lower level in comparison with the adriamycin-entrapping liposome preparation according to the invention.

There is no specific term or condition as to the raw materials for manufacturing liposome preparation according to the invention, but as for phosphatidylcholine, it is preferable to employ the same obtained from egg yolk, in view of its availability and the fact that its physical properties have been studied in greater detailed than those of phosphatidylcholine obtained from other sources.

The adriamycin-entrapping liposome preparation according to the invention carries adriamycin in large amount, so that the relative amount of lipids inevitably dosed can be decreased. Further, because adriamycin is combined with sulfatide in the liposomes, binding thereof to acidic lipids of constituents of cell membranes is effectively suppressed and the accumulation in the heart is also suppressed to a greater extent, so that the manifestation of cardiac toxicity could be suppressed maximally, which allows a dosage of adriamycin in a large amount. When the preparation according to the invention is dosed, the concentration of adriamycin in the blood can be kept at a high level, so that the chances that adriamycin can be taken into tumor tissue increase remarkably. Further, the preparation exhibits these advantageous effects in a well-balanced manner. Therefore, the present invention provides an adriamycin preparation which exhibits its pharmacological effects to the maximum, while keeping its side effects to a minimum.

DETAILED DESCRIPTION OF THE PREFERRED EMBODIMENTS

The invention will now be further explained with reference to Examples and Reference Examples as well as Test Example.

Materials, testing methods, and others to be referred to in such Examples are as follows:

(a) Adriamycin: "Adriacin Inj." (Registered Trademark in Japan); It is marketed by Kyowa Hakko Kogyo Co., Ltd. of Tokyo, Japan.

(b) Phosphatidylcholine: Obtained from egg yolk and purified in accordance with disclosures given in "J. Amer. Oil Chem. Soc." Vol. 42, pages 53–56 (1965).

(c) Cholesterol: Purified product on the market.

(d) Sulfatide: Extracted from bovine brain, purified, and obtained as the sodium salt in accordance with disclosures given in "J. Lipid Res." Vol. 3, pages 483–485 (1962).

(e) Phosphatidylserine: Marketed by Sigma Chemical Co. of St. Louis, U.S.A.

(f) Determination of adriamycin concentration: Determination is made in accordance with the method disclosed in "Cancer Chemother. Report" Vol. 54, pages 89–94 (1970).

(g) Determination of liposome concentration: Determination is made on phosphatidylcholine which is the main constituent of liposomes, with use of reagent "Phospholipids B - Test Wako" (Trademark) marketed by Wako Pure Chemical Industries Co., Ltd. of Osaka, Japan.

(h) Measurement of liposome diameter: Diameter of liposomes is measured by use of a standard calibration curve which is obtained by Sephacryl S-1000 column chromatography with latex particles having four different diameters, marketed by Sekisui Chemical Co., Ltd. of Toyko, Japan and Dow Chemical Co. of Indianapolis, U.S.A., and distribution coefficients (Kav) calculated from each volume of elution peak of the particles.

EXAMPLE 1

Figure 1:
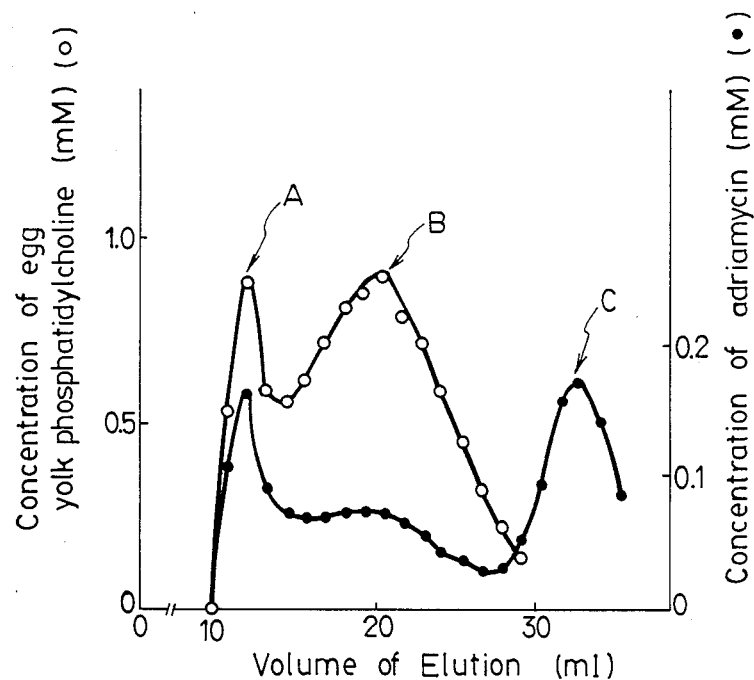
FIG. 1 shows an elution curve on a Sepharose CL-2B column for manufacturing liposome preparations described in Example 1.

An adriamycin-entrapping liposome preparation with multi-layers and adriamycin-entrapping small liposome preparation with a single layer were manufactured with a lipid composition of phosphatidylcholine, cholesterol, and sufatide in a molar ratio of 5:4:1 as follows:

20 $\mu$mol of egg yolk phosphatidylcholine, 16 $\mu$mol of cholesterol, and 4 $\mu$mol of sulfatide were dissolved in chloroform in a round-bottom flask, and treated with a rotary evaporator to remove the solvent under a reduced pressure and to form a lipid film on the inner surface of the flask. The film was dried in vacuo over potassium hydroxide in a desiccator. Then, 4 $\mu$mol of adriamycin in 2 ml of saline was added to the flask, and the solution was shaken under an argon atmosphere to swell the film and to prepare a lipid suspension. The suspension was sonicated at 20 kHz and 30 W for 40 minutes by a probe-type sonicator (Model W-225R, manufactured by Heat Systems-Ultrasonics of Farmingdale, N.Y., U.S.A.) in a 50% pulse mode, and chromatographed at 4° C. with a Sepharose CL-2B (manufactured by Pharmacia of Uppsala, Sweden) column. An elution curve is shown in FIG. 1. As seen from the Figure, large liposomes with multi-layers were firstly eluted near 12 ml, then small liposomes with a single layer near 21 ml, and lastly free adriamycin near 33 ml.

Each of the liposome fractions was collected and concentrated with a Centriflow CF-25 (manufactured by Amicon Corp. of Danvers, U.S.A.) until the concentration of adriamycin reached 0.5 mM.

Figure 2:
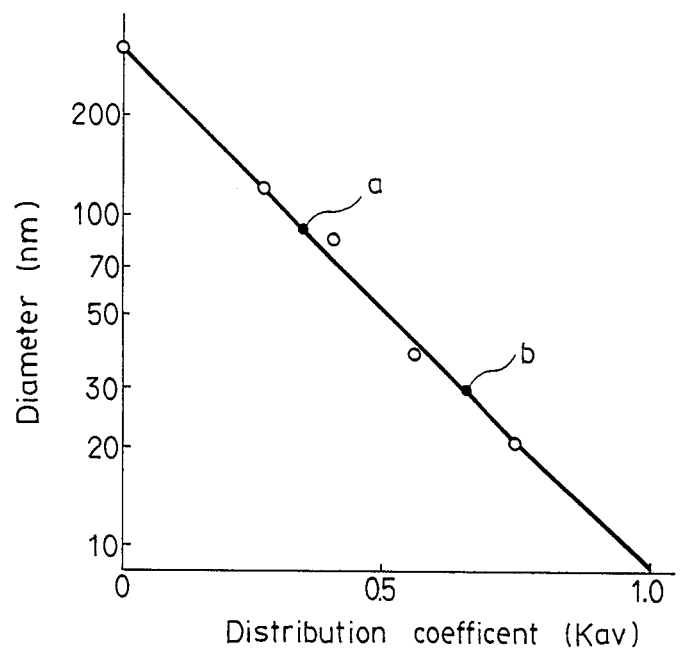
FIG. 2 is a standard calibration curve for determining the diameter of the liposomes, and also shows that the liposome preparations (small liposomes with a single layer and ones with multi-layers) obtained by Example 1 have diameters of about 30 and 85 nm, respectively.

The distribution coefficients (Kav) of the liposomes with multi-layers and of the small liposomes with a single layer were calculated as 0.36 and 0.67, respectively by chromatography with a Sephacryl S-1000 column, each of which values was collated with a standard calibration curve as shown in FIG. 2. The liposomes were shown to have diameters of about 85 and 30 nm, respectively.

The amount of adriamycin entrapped in those liposomes is shown on the first and second lines in Table 1 which will be given later.

EXAMPLE 2

An adriamycin-entrapping liposome preparation in this Example was manufactured in the following manner:

To a mixed lipid solution of egg yolk phosphatidylcholine (20 $\mu$mol), cholesterol (16 $\mu$mol), and sulfatide (4 $\mu$mol), 4 $\mu$mol of adriamycin dissolved in methanol were added and a lipid film comprising adriamycin was prepared on the inner surface of a flask in a similar manner as in Example 1. The film was dried in vacuo over potassium hydroxide in a desiccator and 2 ml of saline was added to the flask. The solution was shaken under an argon atmosphere to swell the film and to prepare a lipid suspension. The suspension was treated as in Example 1 to prepare the liposomes with multi-layers and small liposomes with a single layer, which were separated from free adriamycin. The elution curve in this case was substantially the same as that shown in FIG. 1. The amount of adriamycin entrapped in each of the liposomes was also substantially the same as that in Example 1.

As to Reference Examples given later:

Adriamycin-entrapping liposome preparations, whose liposomes are different from those in the preceding Examples in lipid composition were manufactured according to the following Reference Examples for comparison with those used in the Examples.

REFERENCE EXAMPLE 1

An adriamycin-entrapping liposome preparation, the liposomes of which have a lipid composition low in cholesterol (phosphatidylcholine:cholesterol:sulfatide=7:2:1)

A mixed lipid solution of egg yolk phosphatidylcholine (28 $\mu$mol), cholesterol (8 $\mu$mol), and sulfatide (4 $\mu$mol) was treated as in Example 1 to obtain an adriamycin-entrapping liposome preparation. Almost all of the liposomes had a single layer. The amount of adriamycin entrapped in the liposomes is shown on the third line in Table 1, as given later.

REFERENCE EXAMPLE 2

An adriamycin-entrapping liposome preparation, the liposomes of which have a lipid composition high in cholesterol (phosphatidylcholine:cholesterol:sulfatide=4:5:1)

A mixed lipid solution of egg yolk phosphatidylcholine (16 $\mu$mol), cholesterol (20 $\mu$mol), and sulfatide (4 $\mu$mol) was treated to prepare a lipid suspension in a similar manner as in Example 1. The suspension was sonicated under the conditions as used in Example 1, but it was difficult to form the liposomes. Therefore, the sonication was carried out not in ice water, but in water at room temperature and the gel-filtration chromatography with a Sepharose CL-2B column was also carried out at room temperature to satisfy the conditions for forming the liposomes, but almost all liposomes formed were those with multi-layers. The amount of adriamycin entrapped in the liposomes is shown on the fourth line in Table 1, as given later.

REFERENCE EXAMPLE 3

An adriamycin-entrapping liposome preparation, the liposomes of which have a lipid composition high in sulfatide (phosphatidylcholine:cholesterol:sulfatide=4:4:2)

A mixed lipid solution of egg yolk phosphatidylcholine (16 $\mu$mol), cholesterol (16 $\mu$mol), and sulfatide (4 $\mu$mol) was treated to prepare a lipid suspension in a similar manner as in Example 1. The suspension was sonicated under the same conditions as used in Example 1, but it was difficult to form the liposomes. Therefore, the sonication and gel-filtration chromatography were carried out at room temperature to satisfy the conditions for forming the liposomes, as in Reference Example 2, and almost all liposomes formed were those with multi-layers and having a diameter substantially the same as that of the large liposome preparation obtained in Example 1. The amount of adriamycin entrapped in the liposome preparation of this Reference Example is shown on the fifth line in Table 1, as given later.

REFERENCE EXAMPLE 4

An adriamycin-entrapping liposome preparation, the liposomes of which were formed with lipids of phospatidylcholine, cholesterol, and phosphatidylserine as the acidic phospholipid in lieu of sulfatide as acidic glycolipid, as well as another adriamycin-entrapping liposome preparation, the liposomes of which were formed with lipids of egg yolk phosphatidylcholine and cholesterol only.

These preparations were manufactured in a similar manner as given in Example 1, to compare the same with that according to the present invention. Each preparation obtained in this Reference Example has the liposomes with a single layer. The diameter of the liposomes is substantially the same as that of the small liposome preparation obtained in Example 1. The amount of adriamycin entrapped in the liposome preparations obtained in this Reference Example is shown on the sixth and seventh lines in Table 1, as given later.

TEST EXAMPLE

To male ddY-mice weighing 30 to 35 g, 150nmol of free adriamycin or 150 nmol of adriamycin entrapped in the liposomes described in Examples 1 and 2 as well as in Reference Examples 1, 3, and 4 were dosed through a tail vein of the animal. 30 minutes after the injection, the blood was withdrawn and then each of organs was removed. Each organ was washed with chilled saline and, in the case of the liver, the chilled saline was further used to perfuse it. After having homogenized each organ with five volume of chilled water, an aliquot of the samples was mixed with water to adjust its volume to 2 ml. To the homogenate, 0.8 g of sodium chloride and 4 ml of butanol were added and the resulting solution was heated at 100° C. for 10 minutes, vigorously shaken for 15 minutes, and then centrifuged for 10 minutes at 3000 rpm. Adriamycin extracted in butanol was excited at 470 nm and its fluorescence intensity was measured with a fluorospectrophotometer (Model 650-10S, manufactured by Hitachi Ltd. of Tokyo, Japan) to calculate the amount of adriamycin per weight of each organ. To determine the efficiency of extraction, a known amount of adriamycin was added to each organ homogenate and then extraction was made. The efficiency was about 100%.

Among results obtained by the tests, those on the heart and blood are shown in Table 2, as given later. It can be seen from the Table that the adriamycin-entrapping liposome preparations according to the invention (Examples 1 and 2) satisfy the requirements for increasing the blood concentration of adriamycin and lowering its accumulation in the heart in a better balance than free adriamycin and the adriamycin-entrapping liposome preparations obtained by Reference Examples 1, 3, and 4 and that these characteristics remarkably appear not in small liposome preparations with a single layer but in those with multi-layers.

In the following Tables, please note that abbreviations are as follows and "free adriamycin" indicates adriamycin dissolved in saline and dosed as it were, without entrapping in liposomes.

PC: Phosphatidylcholine,
Chol: Cholestrol, and
PS: Phosphatidylserine

TABLE 1

| Composition of liposomes | Molar ratio | Number of adriamycin molecules entrapped in 1000 molecules of lipids |
|---|---|---|
| PC:Chol:Sulfatide (multi-layers) | 5:4:1 | 81 |
| PC:Chol:Sulfatide (small, single layer) | 5:4:1 | 36 |
| PC:Chol:Sulfatide (small, single layer) | 7:2:1 | 33 |
| PC:Chol:Sulfatide (multi-layers) | 4:5:1 | 66 |
| PC:Chol:Sulfatide (multi-layers) | 4:4:2 | 77 |
| PC:Chol:PS (small, single layer) | 5:4:1 | 17 |
| PC:Chol (small, single layer) | 6:4 | 5 |

TABLE 2

| Composition of liposomes | Molar ratio | Adriamycin uptake (nmol/g or ml ± S.D.) | |
|---|---|---|---|
| | | Heart | Blood |
| PC:Chol:Sulafatide (multi-layers) | 5:4:1 | 2.27 ± 0.54 | 18.2 ± 4.2 |
| PC:Chol:Sulfatide (small, single layer) | 5:4:1 | 4.14 ± 1.08 | 18.3 ± 0.9 |
| PC:Chol:Sulfatide (small, single layer) | 7:2:1 | 4.43 ± 0.59 | 6.00 ± 1.20 |
| PC:Chol:Sulfatide (multi-layers) | 4:4:2 | 0.46 ± 0.09 | 0.07 ± 0.02 |
| PC:Chol:PS (small, single layer) | 5:4:1 | 6.51 ± 0.98 | 4.08 ± 0.90 |
| PC:Chol (small, single layer) | 6:4 | 4.04 ± 0.45 | 2.96 ± 0.56 |
| Free adriamycin | | 7.01 ± 0.78 | 0.45 ± 0.18 |

What is claimed is:

1. An adriamycin-entrapping liposome preparation, comprising lipidic multi-lamellar vesicles containing egg yolk-derived phosphatidylcholine, cholesterol and sulfatide in a molar ratio of 5:4:1.

* * * * *

UNITED STATES PATENT AND TRADEMARK OFFICE
CERTIFICATE OF CORRECTION

PATENT NO. : 4,756,910
DATED : July 12, 1988
INVENTOR(S) : Kunio YAGI et al

It is certified that error appears in the above-identified patent and that said Letters Patent is hereby corrected as shown below:

On the cover page, Item [75], "Nakao Kojma" should read --Nakao Kojima--;

Item [73], "Tokyo, Japan" should read --Gifu, Japan--.

Signed and Sealed this

Thirty-first Day of January, 1989

*Attest:*

DONALD J. QUIGG

*Attesting Officer*  *Commissioner of Patents and Trademarks*